United States Patent [19]
Kim et al.

[11] Patent Number: 5,869,703
[45] Date of Patent: Feb. 9, 1999

[54] NONIONIC VITAMIN E DERIVATIVES AND A METHOD FOR THE PREPARATION THEREOF, AND POLYMERIC AMPLIPHILIC VESICLES MADE THEREFROM

[75] Inventors: Young Dae Kim, Seoul; Jung No Lee; Won Chae Kim, both of Kyunggi-do; Young Hyun Kim; Min Ki Kim, both of Seoul; Myoung Su Ku; Iw Han Cho, both of Seoul, all of Rep. of Korea

[73] Assignee: Pacific Corporation, Seoul, Rep. of Korea

[21] Appl. No.: 959,468

[22] Filed: Oct. 28, 1997

[30] Foreign Application Priority Data

Jul. 12, 1997 [KR] Rep. of Korea .................. 1997-32412

[51] Int. Cl.[6] ........................... C07D 311/72; C08F 20/20
[52] U.S. Cl. ..................... 549/408; 549/410; 549/412; 526/328
[58] Field of Search .................................. 549/408, 410, 549/412; 526/328

[56] References Cited

PUBLICATIONS

Hargreaves et al., "Liposomes from Ionic, Single–Chain Amphiphiles" *Monoalkyl Liposomes* pp. 3759–3760 (1978).
Ohno et al., "Polymerization of Diene–Containing Lipids as Liposomes by Radical Initiators. 4.[1] Effect of Lipid Packing on the Polymerization Profile" *Macromolecules* pp. 319 (1988).
Takeoka et al., "Polymerization of Liposomes Evaluated from Molecular Weight Distribution of Diene–Type Phospholipid Polymers" *Polymer Journal* 22:867–874 (1990).
Chemical Abstract 127:230924–Abst. of Cho et al, Macromol. Symp., 118, pp.631–640 (1997).

*Primary Examiner*—Bernard Dentz
*Attorney, Agent, or Firm*—Foley & Lardner

[57] ABSTRACT

Disclosed herein are nonionic vitamin E or polyethoxylated vitamin E derivatives represented by the following formula (I) and a method for the preparation thereof, and polymeric amphiphilic vesicles made therefrom.

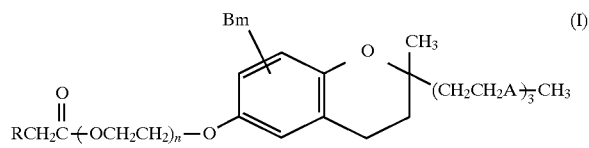

wherein, n is an integer from 0 to 30, inclusive;

A is $-CH_2-CH(CH_3)-$ or $-CH=C(CH_3)-$;

B is $-CH_3$ at the 5-, 7- or 8- position;

m is 1, 2, or 3; and

R is residue of acrylate or methacrylate derivatives represented by the following formula (II);

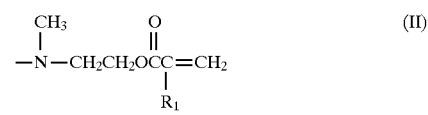

wherein, $R_1$ is H or $CH_3$.

6 Claims, No Drawings

NONIONIC VITAMIN E DERIVATIVES AND A METHOD FOR THE PREPARATION THEREOF, AND POLYMERIC AMPLIPHILIC VESICLES MADE THEREFROM

BACKGROUND OF THE INVENTION

1. Field of the Invention

The present invention relates to nonionic vitamin E derivatives capable of forming polymeric amphiphilic vesicles and to a method for the preparation thereof. More particularly, it relates to nonionic vitamin E or polyethoxylated vitamin E derivatives capable of forming polymeric amphiphilic vesicles which show an excellent thermodynamic stability, a compatibility in the living body and a physiological activity such as anti-oxidative effect, and to a method for the preparation thereof, and to polymeric amphiphilic vesicles made therefrom.

2. Description of the Prior Art

Various oily materials such as triglycerides, fatty acid esters or paraffins have been widely used as emollients in cosmetics and skin ointments for external applications, in order to prevent the evaporation of moisture from the skin. However, the cosmetics or skin ointments containing these oily materials further require an use of surfactants, in order to compensate poor compatibility thereof with water or water miscible components which are used as a base component for the cosmetics and skin ointments.

A surfactant is an amphiphilic or amphiphatic molecule having both a lyophobic group and a lyophilic group. That is, it consists of a long alkyl chain containing polar groups. Also, surfactant show a surface activity in solutions and forms aggregates of molecules or ions which are called micelles, when the concentration of the surfactant solute in the bulk of the solution exceeds a critical value, the so-called critical micelle concentration. The micelles may have spherical, cylindrical or plate shapes and can solubilize water-insoluble materials in the aqueous solution.

Besides, there are many natural amphiphilic biological compounds such as glycolipids, proteins, phospholipids, saponins and bile acids. These compounds are referred to "bio-surfactants", due to their source origin and surface active property. Because of surface activity, they can be easily solubilized in water and the other aqueous solutions so that they may exhibit effectively their physiological activities and make an absorption of other materials easy. In particular, phospholipids are components of the membrane lipid and can form liposomes easily since they have a hydrophobic group consisted of two aliphatic chains. Also, they have an excellent safety and moisture retention activity since they are constituent components of the biological cells. However, phospholipids may be easily oxidized to form peroxides due to the double bondings in the molecule and thereby causing damages to the cells. Consequently, they may promote the aging.

Therefore, there have been extensive studies and discussions for the development of a new material capable of forming vesicles similar to liposome formed by the phospholipids.

Since surfactants can have a vesicle-forming ability only when it has two alkyl chains and a balanced hydrophobic and hydrophilic property, the research for surfactants has been concentrated on the development of synthetic amphiphilic compounds.

J. M. Gebicki and M. Hicks reported in 1975 for the first time the formation of bilayered-membrane structure of the vesicles formed by using synthetic amphiphilic materials. This bilayered-membrane structure was formed by shaking a thin film of oleic acid and linoleic acid in an aqueous buffer. However, this closed membrane structure of bilayer is only stable in pH 6~8 and can not be concentrated by, for example centrifugation.

Thereafter, Kunitake et al. reported vesicles formed by dispersing of dialkyldimethylammonium and dihexadecylphosphate by ultrasonic treatment. The obtained vesicles are stable in the over pH range. However, these synthetic surfactant vesicles have a poor thermodynamic stability and may be easily agglutinated and then precipitated during a long term storage. This restricts the application of synthetic surfactant vesicles.

Recently, the polymerization of vesicles was proposed to improve the stability of synthetic vesicles. Besides, the "ploysoap" which is a polymerized amphiphilic molecules having a single alkyl chain had been also reported.

Therefore, the present inventors have conducted extensive studies to develop new polymeric amphiphilic vesicles. Their studies based on the fact that the vitamin E or polyethoxylated vitamin E derivatives have an excellent compatibility in the living body, surfactantivity, anti-oxidative action such as protective action against oxidation or UV in the skin or hair, and anti-inflammatory action, as well as have a sufficient hydrophobicity and orientation property to be served as hydrophobic group for forming vesicles. As a result, they proposed cationic vitamin E or polyethoxylated vitamin E derivatives obtained by introducing a cationic group of quaternary nitrogen into vitamin E or polyethoxylated vitamin E, and polymeric amphiphilic vesicles made therefrom. As expected, the proposed cationic vitamin E or polyethoxylated vitamin E derivatives have an excellent vesicles-forming ability. However, due to their cationic property, they showed a bad compatibility with anionic or amphipathic components in the living body. On the basis of this failure, they again proposed nonionic vitamin E or polyethoxylated vitamin E derivatives obtained by introducing acrylate, methacrylate or crotonate derivatives into vitamin E or polyethoxylated vitamin E, and polymeric amphiphilic vesicles made therefrom. However, the nonionic derivatives lack an anti-oxidative action preventing the oxidation of physiological active materials.

Under this circumstance, the present inventors have made research to provide a solution for the above problem. As a result, they found that nonionic polymeric amphiphilic vesicles could be obtained by controlling the reaction temperature and the amount of reactants in introducing allyl derivatives containing an amino group into vitamin E or polyethoxylated vitamin E derivatives. They proved that the proposed nonionic vesicles show an excellent thermodynamic stability, a compatibility in the living body and a physiological activity such as anti-oxidative effect.

SUMMARY OF THE INVENTION

Thus, an object of the present invention is to provide nonionic vitamin E or polyethoxylated vitamin E derivatives represented by the following formula (I):

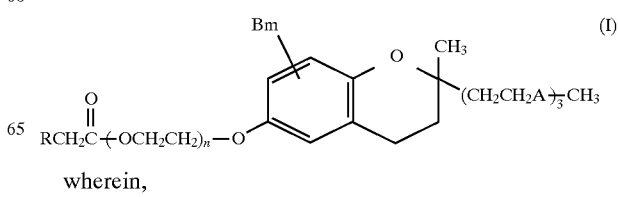

wherein, n is an integer from 0 to 30, inclusive;

A is —CH$_2$—CH(CH$_3$)— or —CH=C(CH$_3$)—;

B is —CH$_3$ at the 5-, 7- or 8- position;

m is 1, 2, or 3 ; and

R is a residue of acrylate or methacrylate derivatives represented by the following formula (II);

$$-\underset{R_1}{N}-CH_2CH_2O\underset{\|}{\overset{O}{C}}\underset{CH_3}{\overset{|}{C}}=CH_2 \quad (II)$$

wherein,

R$_1$ is H or CH$_3$.

A further object of the present invention is to provide a method for the preparation of the nonionic vitamin E or polyethoxylated vitamin E derivatives represented by the formula (I).

A still object of the present invention is to provide polymeric amphiphilic vesicles represented by the following formula (III), which show an excellent thermodynamic stability, a compatibility in the living body and a physiological activity such as anti-oxidative effect:

$$\left[ RCH_2\overset{O}{\underset{\|}{C}}\text{-}(OCH_2CH_2)_n\text{-----}O\underset{}{\overset{Bm}{\diagup}}\overset{CH_3}{\underset{}{\diagdown}}(CH_2CH_2A)_{\overline{3}}\text{-}CH_3 \right]_p \quad (III)$$

wherein, n, A, B, m and R have the same meanings as defined above; and

P indicates a degree of polymerization represented by an integer from 10 to 1,000.

These and other objects and features of the present invention will be apparent to the skilled in the art from the following detailed description.

DETAILED DESCRIPTION OF THE INVENTION

The present invention will be described in more detail hereinafter.

The term "vesicle" used herein means a microspore formed by synthetic surfactant and has the same meaning as a liposome formed by the phospholipids. And, the term "polymeric vesicle" used herein means a vesicle formed by polymerizing said synthetic surfactant.

The method for preparing nonionic vitamin E or polyethoxylated vitamin E derivatives of the present invention comprises steps of (a) reacting the vitamin E or polyethoxylated vitamin E derivatives represented by the following formula (IV) with haloacetic acid or haloacetic anhydride to vitamin E haloacetate or polyethoxylated vitamin E haloacetate derivatives represented by the following formula (V); and $$H(OCH_2CH_2)_n\text{—}O\underset{}{\overset{Bm}{\diagup}}\overset{CH_3}{\underset{}{\diagdown}}(CH_2CH_2A)_3\text{—}CH_3 \quad (IV)$$

$$XCH_2\overset{O}{\underset{\|}{C}}\text{-}(OCH_2CH_2)_n\text{—}O\underset{}{\overset{Bm}{\diagup}}\overset{CH_3}{\underset{}{\diagdown}}(CH_2CH_2A)_{\overline{3}}CH_3 \quad (V)$$

wherein,

B, n and m have the same meanings as defined above;

A is —CH$_2$CH— or —CH=C—; and

X is F, Cl, Br or I.

(b) reacting the vitamin E haloacetate or polyethoxylated vitamin E haloacetate derivatives of the formula (V) of step (a) with acrylate or methacrylate derivatives represented by the following formula (VI) in a mole ratio of 1: 1.5 or more in aprotic solvent, at a temperature of 100°~200° C.;

$$\underset{CH_3}{\overset{CH_3}{\underset{|}{N}}}-CH_2CH_2O\overset{O}{\underset{\|}{C}}\underset{R_1}{\overset{|}{C}}=CH_2 \quad (VI)$$

wherein,

R$_1$ has the same meanings as defined above.

Vitamin E employed in the above method may contain synthetic or natural vitamin E, for example extracted from the seed of plants. Synthetic vitamin E may include, but not limited thereto, dl-α-tocopherol, dl-,β-tocopherol. dl-γ-tocopherol and dl-δ-tocopherol.

Further, the polyethoxylated vitamin E derivatives having 1~30 moles of ethylene oxide contained therein may be preferably employed in consideration of the solubility of polymeric amphiphilic vesicles in water, and the fluidity and crystallinity for regular arrangement.

It is preferable to react the compound (V) with the compound (VI) in a mole ratio of 1:1.5 or more. The excessive amount of the compound (VI) may accellerate the nucleophilic substitution in the step (b). Further, in order to facilitate this substitution, the reaction may be preferably carried out in an aprotic solvent. The examples of the aprotic solvent may include, but not limited thereto, dioxane, dimethylformamide(DMF) and tetrahydrofuran(THF).

Further, it is important to carry out the reaction of the step (b) at the temperature of 100°~200° C. and preferably at the temperature of 120°~170° C.

The polymeric amphiphilic vesicles of formula (III) may be obtained by dispersing the nonionic vitamin E derivatives of the present invention or preferably by ultrasonic treatment and then, if preferable, following by the polymerization of the nonionic vitamin E derivatives.

The polymerization of nonionic vitamin E derivatives may be carried out with a free radical initiator at a temperature of 50°~80° C., or may be carried out by an ultraviolet radiation.

The free radical initiator employed in this polymerization may include, but not limited thereto, potassium persulfate ($K_2S_2O_8$), hydrogen peroxide($H_2O_2$), azoisobutyronitile (AIBN) and azobis(4-cyanovaleric acid).

The compound (I) provided by the above method has structure combined hydrophobic group of vitamin E or polyethoxylated vitamin E derivatives with tertiary amine group for the polymerization. Due to this structure, the compound (I) can form vesicles by the ultrasonic dispersion, cylinder injection, etc. In particular, the compound(I) can be easily polymerized by the radical polymerization or ultraviolet radiation since it has double bonds for the polymerization. Further, the polymerized vesicles are more stable than the vesicle monomers.

When the polymeric amphiphilic vesicles of the present invention are incorporated into the cosmetics or pharmaceutical composition, they show a good compatibility with active water-soluble components contained therein and can improve the various activities of components by increasing their affinity with skin, due to their surface activities and vesicle-forming ability. In addition, the polymeric amphiphilic vesicles of the present invention show a further improved anti-oxidative action and moisture retention than vitamin E. These improved anti-oxidative action can effectively prevent the physiological active materials and biological membranes from the oxidations and thereby can retard the skin aging. Further, the improved moisture retention action renders an efficient suppression of the skin's wrinkling, thereby retarding the skin aging.

PREFERRED EMBODIMENTS OF THE INVENTION

The present invention will be illustrated in more detail by way of the following Examples. The following Examples are merely illustrative and it should be understood that the present invention is not limited to these Examples.
(1) Synthesis of Vitamin E haloacetate

EXAMPLE 1

Synthesis of Vitamin E Chloroacetate 10 g (23.2 mmol) of synthetic vitamin E(dl-α tocopherol) and 4.0 g(39.4 mmol) of triethylamine were dissolved in 70 ml of chloroform and thereto was added dropwise 5.14 g(30.0 mmol) of chloroacetic anhydride under stirring in an ice bath. After addition, the reaction was carried at room temperature for 4 hour. Then, the reaction solution was washed with 50 ml of water, with 100 ml of 5% sodium bicarbonate($NaHCO_3$) solution and with 50 ml of water, in this order. After washing, the mixture was dried over sodium sulfate($Na_2SO_4$) and then distilled under reduced pressure to give 9.5 g of vitamin E chloroacetate(yield; 84.0%).

EXAMPLE 2

Synthesis of Vitamin E Bromoacetate 10 g (23.2 mmol) of synthetic vitamin E(dl-α tocopherol) and 3.0 g(29.7 mmol) of triethylamine were dissolved in 60 ml of chloroform and thereto was added dropwise 4.5 g(28.7 mmol) of bromoacetylchloride under stirring in an ice bath. After addition, the reaction was carried at room temperature for 3 hour. Then, the reaction solution was washed with 100 ml of water, with 70 ml of 5% sodium bicarbonate ($NaHCO_3$) solution and with 100 ml of water, in this order. After washing, the mixture was dried over sodium sulfate ($Na_2SO_4$) and then distilled under reduced pressure to give 11.5 g of vitamin E bromoacetate(yield; 89.8%).

EXAMPLE 3

Synthesis of Polyethoxylated Vitamin E Chloroacetate 10 g (11.5 mmol) of polyethoxylated vitamin E(n=10) and 3.5 g(34.6 mmol) of triethylamine were dissolved in 60 ml of chloroform and thereto was added dropwise 5.0 g(29.2 mM) of chloroacetic anhydride under stirring in an ice bath. After addition, the reaction was carried at room temperature for 4 hour. Then, the reaction solution was washed with 110 ml of water, with 70 ml of 5% sodium bicarbonate ($NaHCO_3$) solution and with 110 ml of water, in this order. After washing, the mixture was dried over sodium sulfate ($Na_2SO_4$) and then distilled under reduced pressure to give 11.2 g of polyethoxylated vitamin E chloroacetate(yield; 92.0%).
(2) Synthesis of nonionic vitamin E derivatives

EXAMPLE 4

20.0 g (21.1 mmol) of polyethoxylated vitamin E chloroacetate(n=10) prepared in Example 3 and 6.5 g(41.3 mmol) of 2-(dimethylamino)ethylmetacrylate were dissolved in anhydrous dimethylformamide, and heated and refluxed at 150° C. for 24 hours. The resulting suspension was heated under vacuum to remove solvent and purified by the silica gel column with mixed solvent of hexan-ethylacetate to give 17.9 g of nonionic vitamin E derivatives of the formula (I) (yield; 80.5%). The structure of product was identified by $^1$H NMR and IR.

$^1$H NMR($CDCl_3$): δ(ppm), 6.10–5.54 (s. 2H), 4.42–3.61 (m. 42H), 3.40(s. 2H), 2.94–2.88 (t. 2H), 2.56 (s. 3H), 2.47(s. 3H), 2.15 (s. 3H), 2.11(s, 3H), 1.90–1.50 (m. 21H), 1.3–0.95 (m. 21H), 0.67–0.59 (m. 12H)

IR(KBr); 2927(—C—H), 1759(—C=O), 1638(—C=C—), 1158(—C—O—) $cm^{-1.}$

EXAMPLE 5

10.0 g (19.6 mmol) of vitamin E chloroacetate prepared in Example 1 and 5.6 g(29.2 mmol) of 2-(dimethylamino) ethylmetacrylate were dissolved in anhydrous tetrahydrofiran, and heated and refluxed at 125° C. for 48 hours. The resulting suspension was heated under vacuum to remove solvent and purified by the silica gel column with mixed solvent of hexan-ethylacetate to give 7.8 g of nonionic vitamin E derivatives of the formula (I) (yield; 66.1%).

EXAMPLE 6

The procedure described in Example 5 was followed by employing vitamin E bromoacetate prepared in Example 2, instead of vitamin E chloroacetate, to give nonionic vitamin E derivatives of the formula (I)(yield; 71.6%).

EXAMPLE 7

The procedure described in Example 5 was followed by employing polyethoxylated vitamin E chloroacetate(n=20), instead of vitamin E chloroacetate, to give nonionic vitamin E derivatives of the formula (I)(yield; 76.2%).

EXAMPLE 8

10.0 g (19.6 mmol) of vitamin E chloroacetate prepared in Example 1 and 6.2 g(39.2 mmol) of 2-(dimethylamino) ethylacrylate were dissolved in anhydrous dimethylformamide, and heated and refluxed at 170° C. for 48 hours. The resulting suspension was heated under vacuum to remove solvent and purified by the silica gel column with mixed solvent of hexan-ethylacetate to give nonionic vitamin E derivatives of the formula (I) (yield; 78.3%).

EXAMPLE 9

The procedure described in Example 8 was followed by employing vitamin E bromoacetate prepared in Example 2, instead of vitamin E chloroacetate, to give nonionic vitamin E derivatives of the formula (I)(yield; 45.0%).

EXAMPLE 10

The procedure described in Example 8 was followed by employing tetrahydrofuran, instead of anhydrous dimethylformamide, to give nonionic vitamin E derivatives of the formula (I)(yield; 58.0%).

(3) Synthesis of polymeric amphiphilic vesicles

EXAMPLE 11

Polymeric Amphiphilic Vesicles Polymerized in Water 0.2 g of nonionic vitamin E derivative prepared in Example 4 was ultrasonic dispersed in 50 ml of deionized water. Then, the polymerization was carried out in the present of 4 mg of potassium persulfate($K_2S_2O_8$) under stirring at 65° C., to give polymeric amphiphilic vesicles containing tocopherol. This polymerization was performed under nitrogen atmosphere so as to prevent oxidation.

The polymerization proceed very slowly which is thought to be due to large size of hydrophobic group and thereby to weak hydrophilic property.

The formed polymeric amphiphilic vesicles were observed with photomicrograph and TEM(JEOL. TEM-100 cx). The result are that they have closed ellipsoidal shape having short diameter of 300~1,200 Å and long diameter of 600~2,300 Å.

EXAMPLE 12

Polymeric Amphiphilic Vesicles Polymerized in Ethanol 0.2 g of nonionic vitamin E derivative prepared in Example 5 was ultrasonic dispersed in 50 ml of 4% ethanol solution. Then, the polymerization was carried out in the present of 2 mg of azoisobutyronitile(AIBN). This polymerization was performed under nitrogen atmosphere to prevent oxidation under heating to 80° C. The formed polymeric amphiphilic vesicles was confirmed by $^1$H-NMR, $^{13}$C—NMR(CDCl$_3$) and IR.

$^1$H NMR(CDCl$_3$): δ (ppm), 6.10–5.54 (s. 2H), 4.33–4.27 (t. 2H), 3.67(s. 2H), 3.02–2.96 (t. 2H), 2.56 (s. 6H), 2.15(s. 3H), 2.11 (s. 3H), 2.0(s, 3H), 1.90–1.50 (m. 2H), 1.3–0.95 (m. 21H), 0.67–0.59 (m. 12H)

$^{13}$C—NMR(CDCl$_3$); δ 169.6, 167.3(—C=O—), δ 149.5 (—C=),

δ 125.6(=CH$_2$), δ 75.1, 62.9, 58.2, 55.0(keto-six membered ring),

δ 140.2, 136.2, 126.5, 124.8, 123.1, 117.4(benzene), δ 75.1, 62.9, 58.2, 55.0(oxane ring α carbon, N—CH$_2$—C(=O)—), —N—CH$_2$—CH$_2$—O—), δ 2.5, 29.4, 37.6, 37.5, 37.4, 37.3, 32.8, 32.7, 31.0, 27.9, 24.8, 24.5, 22.7, 22.6, 21.0, 20.6, 19.8, 19.7, 19.6, 19.5, 19.3, 13.1, 12.2, 11.8

IR (KBr); 2927(—C—H), 1759(—C=O), 1638(—C=C—), 1158(—C—O—)

<Experimental Example 1> Stability against heating

The polymeric amphiphilic vesicles prepared in Examples 11 and 12 were stable at room temperature for 8 months or more. Also, the vesicles with heating treatment to 45° C. were stable at room temperature for 3 months or more.

<Experimental Example 2> Anti-oxidative activity

Anti-oxidation activity was evaluated for nonionic vitamin E derivatives prepared Examples 4 and 5 and polymeric amphiphilic vesicles prepared in Examples 11 and 12 according to the following two method. Also, this experiment was applied to vitamin E, vitamin E acetate, soybean lecithin and dipalmitoyl phosphatidylcholine, in order to compare the activities.

<Experimental Example 2-1> Anti-oxidative activity using DPPH

Diphenylpicrylhydrazyl(DPPH) has been known as a radical reaction inhibitor which is stabilized by the radical reaction. Also, it and has chromophoric property with compound having anti-oxidative activity. Therefore, this experiment utilized the above property.

About 50 ml of DPPH was introduced into the test tube. And samples were added dropwise thereto. After addition, the test tube was maintained in constant temperature bath of 37° C. for 30 minutes. The extent of color development was measured by UV spectrophotometer. The results are shown in Table 1.

<Experimental Example 2-2> Anti-oxidative activity using linoleic acid

Linoleic acid is easily oxidized to be peroxide due to double bond contained therein. Therefore, this experiment utilized the above property.

The control solution employed in this experiment was prepared by adding 2.88 ml of 2.5% linoeic acid in ethanol and 9 ml of 40 mmol phosphate buffer(pH7.0) to 120 ml of ethanol. This control solution was maintained in the dark of 40° C.

And, sample solutions were prepared by adding 9.7 ml of 75% ethanol, 0.1 ml of 30% amoniumthiocyanate and 0.1 ml of each sample, to 0.1 ml of the control solution.

After 3 minutes, the absorbance was measured at 50 nm by using UV spectrophotometer. Lower absorbance value means higher anti-oxidative activity. The results are shown in Table 1.

TABLE 1

| Sample | Experimental Example 2-1 color change of DPPH | Experimental Example 2-2 absorbance (50 nm) |
|---|---|---|
| Control* | brown | 0.17 |
| Vitamin E derivative of Example 4 | brown | 0.33 |
| Polymeric amphiphilic vesicle of Example 10 | brown | 0.45 |
| Vitamin E derivative of Example 5 | brown | 0.27 |
| Polymeric amphiphilic vesicle of Example 11 | brown | 0.41 |

TABLE 1-continued

| Sample | Experimental Example 2-1 color change of DPPH | Experimental Example 2-2 absorbance (50 nm) |
|---|---|---|
| Vitamin E | brown | 0.25 |
| Vitamin E acetate | no color change | 0.45 |
| Soybean lecithin | no color change | 0.61 |
| Dipalmitoyl phosphatidylcholine | no color change | 0.44 |

*For Experiment 2-1, control was DPPH solution containing no samples.

As shown in table 1, vitamin E derivatives of the present invention show an anti-oxidative activity which is similar to that of vitamin E. Also, their polymeric amphiphilic vesicles show an anti-oxidative activity which is slightly lower than that of vitamin E, but higher than that of control.

What is claimed is:

1. Nonionic vitamin E or polyethoxylated vitamin E derivatives represented by the following formula (I);

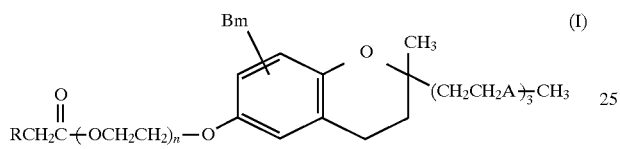

wherein, n is an integer from 0 to 30, inclusive;

A is —CH$_2$—CH(CH$_3$)— or —CH═C(CH$_3$)—;

B is —CH$_3$ at the 5-, 7- or 8- position;

m is 1, 2, or 3; and

R is a residue of acrylate or methacrylate derivatives represented by the following formula (II);

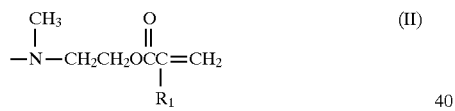

wherein,

R$_1$ is H or CH$_3$.

2. Polymeric amphiphilic vesicles represented by the following formula (III) and prepared by a polymerization of nonionic vitamin E or polyethoxylated vitamin E derivatives of claim 1

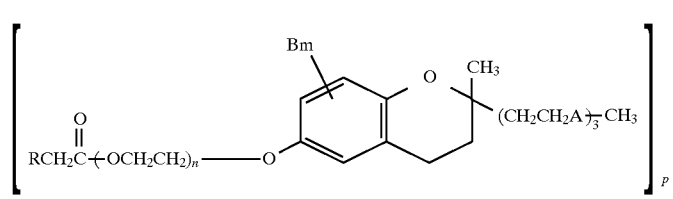

wherein n, A, B, m and R have the same meanings as defined in claim 1; and

P indicates a degree of polymerization represented by an integer from 10 to 1,000.

3. A method for preparing nonionic vitamin E or polyethoxylated vitamin E derivatives of claim 1 which comprises;

(a) reacting the vitamin E or polyethoxylated vitamin E derivatives represented by the following formula (IV) with haloacetic acid or haloacetic anhydride to vitamin E haloacetate polyethoxylated vitamin E haloacetate derivatives represented by the following formula (V);

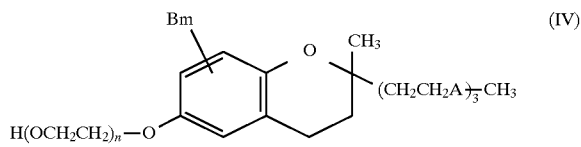

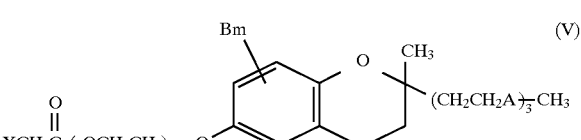

wherein,

A, n and m have the same meanings as defined in claim 1 and;

X is F, Cl, Br or I, (b) reacting the vitamin E haloacetate or polyethoxylated vitamin E haloacetate derivatives of the formula (V) of step (a) with acrylate or methacrylate derivatives represented by the following formula (VI) in a mole ratio of 1: 1.5 or more in an aprotic solvent, at a temperature of 100°~200° C.;

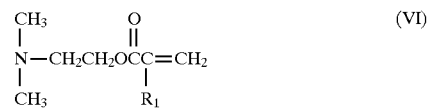

wherein,

R$_1$ has the same meanings as defined in claim 1.

4. The method claimed in claim 3, wherein said vitamin E is selected from the group consisting of synthetic vitamin E and natural vitamin E.

5. The method claimed in claim 4, wherein said synthetic vitamin E is selected from the group of consisting of dl- α tocopherol, dl-β tocopherol, dl-γ tocopherol and dl-δ tocopherol.

6. The method claimed in claim 3, wherein said aprotic solvent in said step (b) is selected from the group consisting of dioxane, dimethylformamide and tetrahydrofuran.

* * * * *